United States Patent
Eisinger

(10) Patent No.: US 11,690,624 B2
(45) Date of Patent: Jul. 4, 2023

(54) RELOAD ASSEMBLY INJECTION MOLDED STRAIN GAUGE

(71) Applicant: Covidien LP, Mansfield, MA (US)

(72) Inventor: Joseph Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 118 days.

(21) Appl. No.: 16/448,485

(22) Filed: Jun. 21, 2019

(65) Prior Publication Data
US 2020/0397439 A1     Dec. 24, 2020

(51) Int. Cl.
*A61B 17/00* (2006.01)
*A61B 17/115* (2006.01)
*A61B 17/10* (2006.01)
*A61B 17/072* (2006.01)

(52) U.S. Cl.
CPC ........ *A61B 17/1155* (2013.01); *A61B 17/105* (2013.01); *A61B 2017/00526* (2013.01); *A61B 2017/07285* (2013.01); *A61B 2562/0261* (2013.01)

(58) Field of Classification Search
CPC .............. A61B 17/1155; A61B 17/105; A61B 2562/0261; A61B 2017/00526; A61B 2017/07285; A61B 2017/00836; A61B 2017/00734; A61B 2017/00115; A61B 2017/07257; A61B 2017/00039; A61B 2017/00862
USPC ........................................... 227/175.1–182.1
See application file for complete search history.

(56) References Cited

U.S. PATENT DOCUMENTS

| | | | |
|---|---|---|---|
| 3,193,165 A | | 7/1965 | Akhalaya et al. |
| 3,388,847 A | | 6/1968 | Kasulin et al. |
| 3,552,626 A | | 1/1971 | Astafiev et al. |
| 3,638,652 A | | 2/1972 | Kelley |
| 3,771,526 A | | 11/1973 | Rudie |
| 3,986,254 A | * | 10/1976 | Nordstrom ............... G01B 7/18 29/613 |
| 4,066,133 A | * | 1/1978 | Voss ..................... B25B 23/147 73/862.23 |
| 4,198,982 A | | 4/1980 | Fortner et al. |
| 4,207,898 A | | 6/1980 | Becht |
| 4,289,133 A | | 9/1981 | Rothfuss |
| 4,304,236 A | | 12/1981 | Conta et al. |
| 4,319,576 A | | 3/1982 | Rothfuss |
| 4,350,160 A | | 9/1982 | Kolesov et al. |

(Continued)

FOREIGN PATENT DOCUMENTS

CA     908529 A      8/1972
CA     2805365 A1    8/2013
(Continued)

OTHER PUBLICATIONS

European Search Report dated Nov. 16, 2020, issued in corresponding EP Appln. No. 20180349, 9 pages.

*Primary Examiner* — Robert F Long
(74) *Attorney, Agent, or Firm* — Carter, DeLuca & Farrell LLP

(57) ABSTRACT

A surgical stapling device includes a reload assembly that includes a shell housing, a staple cartridge, a plurality of staples received within the staple cartridge, a staple pushing member for ejecting the plurality of staples from the staple cartridge, and a knife for cutting tissue. The shell housing supports a strain gauge which can be molded into the shell housing.

6 Claims, 5 Drawing Sheets

(56) References Cited

U.S. PATENT DOCUMENTS

| | | |
|---|---|---|
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,738,140 A * | 4/1988 | Kempf ................ G01L 5/1627 73/753 |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,217,478 A * | 6/1993 | Rexroth ............ A61B 17/32002 606/180 |
| 5,221,036 A | 6/1993 | Takase |
| 5,222,963 A | 6/1993 | Brinkerhoff et al. |
| 5,247,172 A * | 9/1993 | Riemer ................ F15B 15/28 250/227.21 |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,389,098 A * | 2/1995 | Tsuruta ............ A61B 17/07207 606/49 |
| 5,392,979 A | 2/1995 | Green et al. |
| 5,395,030 A | 3/1995 | Kuramoto et al. |
| 5,395,033 A * | 3/1995 | Byrne ............ A61B 17/07207 227/175.1 |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,792,165 A * | 8/1998 | Klieman ............ A61B 34/71 606/174 |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |

(56) References Cited

U.S. PATENT DOCUMENTS

| | | | |
|---|---|---|---|
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,361,542 B1 | 3/2002 | Dimitriu et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,740,058 B2 * | 5/2004 | Lal ..................... A61F 9/00745 604/65 |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,188,535 B1 * | 3/2007 | Spletzer ............... G01L 1/2206 73/862.041 |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |

(56) References Cited

U.S. PATENT DOCUMENTS

| | | | |
|---|---|---|---|
| 7,886,951 | B2 | 2/2011 | Hessler |
| 7,896,215 | B2 | 3/2011 | Adams et al. |
| 7,900,806 | B2 | 3/2011 | Chen et al. |
| 7,909,039 | B2 | 3/2011 | Hur |
| 7,909,219 | B2 | 3/2011 | Cole et al. |
| 7,909,222 | B2 | 3/2011 | Cole et al. |
| 7,909,223 | B2 | 3/2011 | Cole et al. |
| 7,913,892 | B2 | 3/2011 | Cole et al. |
| 7,918,377 | B2 | 4/2011 | Measamer et al. |
| 7,922,062 | B2 | 4/2011 | Cole et al. |
| 7,922,743 | B2 | 4/2011 | Heinrich et al. |
| 7,931,183 | B2 | 4/2011 | Orban, III |
| 7,938,307 | B2 | 5/2011 | Bettuchi |
| 7,942,302 | B2 | 5/2011 | Roby et al. |
| 7,951,166 | B2 | 5/2011 | Orban, III et al. |
| 7,959,050 | B2 | 6/2011 | Smith et al. |
| 7,967,181 | B2 | 6/2011 | Viola et al. |
| 7,975,895 | B2 | 7/2011 | Milliman |
| 8,002,795 | B2 | 8/2011 | Beetel |
| 8,006,701 | B2 | 8/2011 | Bilotti et al. |
| 8,006,889 | B2 | 8/2011 | Adams et al. |
| 8,011,551 | B2 | 9/2011 | Marczyk et al. |
| 8,011,554 | B2 | 9/2011 | Milliman |
| 8,016,177 | B2 | 9/2011 | Bettuchi et al. |
| 8,016,858 | B2 | 9/2011 | Whitman |
| 8,020,741 | B2 | 9/2011 | Cole et al. |
| 8,025,199 | B2 | 9/2011 | Whitman et al. |
| 8,028,885 | B2 | 10/2011 | Smith et al. |
| 8,038,046 | B2 | 10/2011 | Smith et al. |
| 8,043,207 | B2 | 10/2011 | Adams |
| 8,066,167 | B2 | 11/2011 | Measamer et al. |
| 8,066,169 | B2 | 11/2011 | Viola |
| 8,070,035 | B2 | 12/2011 | Holsten et al. |
| 8,070,037 | B2 | 12/2011 | Csiky |
| 8,096,458 | B2 | 1/2012 | Hessler |
| 8,109,426 | B2 | 2/2012 | Milliman et al. |
| 8,109,427 | B2 | 2/2012 | Orban, III |
| 8,113,405 | B2 | 2/2012 | Milliman |
| 8,113,406 | B2 | 2/2012 | Holsten et al. |
| 8,113,407 | B2 | 2/2012 | Holsten et al. |
| 8,118,206 | B2* | 2/2012 | Zand .............. A61B 5/14556 227/175.1 |
| 8,123,103 | B2 | 2/2012 | Milliman |
| 8,128,645 | B2 | 3/2012 | Sonnenschein et al. |
| 8,132,703 | B2 | 3/2012 | Milliman et al. |
| 8,136,712 | B2 | 3/2012 | Zingman |
| 8,146,790 | B2 | 4/2012 | Milliman |
| 8,146,791 | B2 | 4/2012 | Bettuchi et al. |
| 8,181,838 | B2 | 5/2012 | Milliman et al. |
| 8,192,460 | B2 | 6/2012 | Orban, III et al. |
| 8,201,720 | B2 | 6/2012 | Hessler |
| 8,203,782 | B2 | 6/2012 | Brueck et al. |
| 8,211,130 | B2 | 7/2012 | Viola |
| 8,225,799 | B2 | 7/2012 | Bettuchi |
| 8,225,981 | B2 | 7/2012 | Criscuolo et al. |
| 8,231,041 | B2 | 7/2012 | Marczyk et al. |
| 8,231,042 | B2 | 7/2012 | Hessler et al. |
| 8,257,391 | B2 | 9/2012 | Orban, III et al. |
| 8,267,301 | B2 | 9/2012 | Milliman et al. |
| 8,272,552 | B2 | 9/2012 | Holsten et al. |
| 8,276,802 | B2 | 10/2012 | Kostrzewski |
| 8,281,975 | B2 | 10/2012 | Criscuolo et al. |
| 8,286,845 | B2 | 10/2012 | Perry et al. |
| 8,308,045 | B2 | 11/2012 | Bettuchi et al. |
| 8,312,885 | B2 | 11/2012 | Bettuchi et al. |
| 8,313,014 | B2 | 11/2012 | Bettuchi |
| 8,317,073 | B2 | 11/2012 | Milliman et al. |
| 8,317,074 | B2 | 11/2012 | Ortiz et al. |
| 8,322,590 | B2 | 12/2012 | Patel et al. |
| 8,328,060 | B2 | 12/2012 | Jankowski et al. |
| 8,328,062 | B2 | 12/2012 | Viola |
| 8,328,063 | B2 | 12/2012 | Milliman et al. |
| 8,343,185 | B2 | 1/2013 | Milliman et al. |
| 8,353,438 | B2 | 1/2013 | Baxter, III et al. |
| 8,353,439 | B2 | 1/2013 | Baxter, III et al. |
| 8,353,930 | B2 | 1/2013 | Heinrich et al. |
| 8,360,295 | B2 | 1/2013 | Milliman et al. |
| 8,365,974 | B2 | 2/2013 | Milliman |
| 8,403,942 | B2 | 3/2013 | Milliman et al. |
| 8,408,441 | B2 | 4/2013 | Wenchell et al. |
| 8,413,870 | B2 | 4/2013 | Pastorelli et al. |
| 8,413,872 | B2 | 4/2013 | Patel |
| 8,418,905 | B2 | 4/2013 | Milliman |
| 8,418,909 | B2 | 4/2013 | Kostrzewski |
| 8,424,535 | B2 | 4/2013 | Hessler et al. |
| 8,424,741 | B2 | 4/2013 | McGuckin, Jr. et al. |
| 8,430,291 | B2 | 4/2013 | Heinrich et al. |
| 8,430,292 | B2 | 4/2013 | Patel et al. |
| 8,453,910 | B2 | 6/2013 | Bettuchi et al. |
| 8,453,911 | B2 | 6/2013 | Milliman et al. |
| 8,485,414 | B2 | 7/2013 | Criscuolo et al. |
| 8,490,853 | B2 | 7/2013 | Criscuolo et al. |
| 8,511,533 | B2 | 8/2013 | Viola et al. |
| 8,529,599 | B2* | 9/2013 | Holsten .............. A61B 17/0682 606/219 |
| 8,551,138 | B2 | 10/2013 | Orban, III et al. |
| 8,567,655 | B2 | 10/2013 | Nalagatla et al. |
| 8,579,178 | B2 | 11/2013 | Holsten et al. |
| 8,590,763 | B2 | 11/2013 | Milliman |
| 8,590,764 | B2 | 11/2013 | Hartwick et al. |
| 8,608,047 | B2 | 12/2013 | Holsten et al. |
| 8,613,230 | B2* | 12/2013 | Blumenkranz ........ A61B 34/37 73/862.044 |
| 8,616,428 | B2 | 12/2013 | Milliman et al. |
| 8,616,429 | B2 | 12/2013 | Viola |
| 8,622,275 | B2 | 1/2014 | Baxter, III et al. |
| 8,622,935 | B1* | 1/2014 | Leo ...................... A61B 5/0084 604/95.01 |
| 8,631,993 | B2 | 1/2014 | Kostrzewski |
| 8,636,187 | B2 | 1/2014 | Hueil et al. |
| 8,640,940 | B2 | 2/2014 | Ohdaira |
| 8,662,370 | B2 | 3/2014 | Takei |
| 8,663,258 | B2 | 3/2014 | Bettuchi et al. |
| 8,672,931 | B2 | 3/2014 | Goldboss et al. |
| 8,678,264 | B2 | 3/2014 | Racenet et al. |
| 8,684,248 | B2 | 4/2014 | Milliman |
| 8,684,250 | B2 | 4/2014 | Bettuchi et al. |
| 8,684,251 | B2 | 4/2014 | Rebuffat et al. |
| 8,684,252 | B2 | 4/2014 | Patel et al. |
| 8,709,012 | B2* | 4/2014 | Muller ............... A61B 17/1666 606/79 |
| 8,733,611 | B2 | 5/2014 | Milliman |
| 8,862,209 | B2* | 10/2014 | Whitman .............. A61B 17/115 600/478 |
| 9,055,962 | B2* | 6/2015 | Blumenkranz ........ G02B 6/264 |
| 9,636,112 | B2* | 5/2017 | Penna ................. H05K 7/1427 |
| 9,655,616 | B2* | 5/2017 | Aranyi .............. A61B 17/07207 |
| 9,724,094 | B2* | 8/2017 | Baber .............. A61B 17/07292 |
| 9,883,860 | B2* | 2/2018 | Leimbach ............. A61B 34/76 |
| 10,016,199 | B2* | 7/2018 | Baber .................. A61B 90/98 |
| 10,492,814 | B2* | 12/2019 | Snow ................. A61B 17/068 |
| 11,172,580 | B2* | 11/2021 | Gaertner, II ......... H05K 1/0213 |
| 11,424,027 | B2* | 8/2022 | Shelton, IV ......... A61B 17/072 |
| 2002/0165541 | A1* | 11/2002 | Whitman ................ A61N 7/02 606/51 |
| 2003/0111507 | A1 | 6/2003 | Nunez |
| 2004/0073090 | A1 | 4/2004 | Butler et al. |
| 2005/0051597 | A1 | 3/2005 | Toledano |
| 2005/0107813 | A1 | 5/2005 | Gilete Garcia |
| 2005/0131390 | A1* | 6/2005 | Heinrich ............. A61B 17/062 606/1 |
| 2006/0000869 | A1 | 1/2006 | Fontayne |
| 2006/0011698 | A1 | 1/2006 | Okada et al. |
| 2006/0020213 | A1* | 1/2006 | Whitman ................. A61B 1/05 600/478 |
| 2006/0097025 | A1* | 5/2006 | Milliman ............. A61B 17/115 227/175.1 |
| 2006/0201989 | A1 | 9/2006 | Ojeda |
| 2006/0273135 | A1* | 12/2006 | Beetel ............. A61B 17/07207 227/175.1 |
| 2007/0027473 | A1 | 2/2007 | Vresh et al. |
| 2007/0029363 | A1 | 2/2007 | Popov |
| 2007/0060952 | A1 | 3/2007 | Roby et al. |

(56) References Cited

U.S. PATENT DOCUMENTS

| | | | |
|---|---|---|---|
| 2007/0151390 A1* | 7/2007 | Blumenkranz | A61B 34/71 74/490.06 |
| 2007/0179408 A1* | 8/2007 | Soltz | A61B 90/06 600/587 |
| 2008/0164296 A1* | 7/2008 | Shelton | A61B 17/07207 227/175.1 |
| 2008/0216704 A1* | 9/2008 | Eisenbeis | H05K 3/285 106/14.05 |
| 2008/0221598 A1* | 9/2008 | Dlugos | A61F 5/0003 606/157 |
| 2008/0255629 A1* | 10/2008 | Jenson | A61N 1/056 607/19 |
| 2009/0054908 A1* | 2/2009 | Zand | A61B 5/0261 600/300 |
| 2009/0057369 A1* | 3/2009 | Smith | A61B 17/1155 227/175.1 |
| 2009/0090763 A1* | 4/2009 | Zemlok | A61B 90/98 227/175.2 |
| 2009/0234248 A1* | 9/2009 | Zand | A61B 5/0031 600/587 |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2009/0248041 A1* | 10/2009 | Williams | A61B 8/12 606/130 |
| 2010/0019016 A1 | 1/2010 | Edoga et al. | |
| 2010/0051668 A1 | 3/2010 | Milliman et al. | |
| 2010/0084453 A1 | 4/2010 | Hu | |
| 2010/0096435 A1* | 4/2010 | Fuchs | A61B 17/1114 227/179.1 |
| 2010/0147923 A1 | 6/2010 | D'Agostino et al. | |
| 2010/0163598 A1 | 7/2010 | Belzer | |
| 2010/0192705 A1* | 8/2010 | Chu | B25B 23/14 73/862.338 |
| 2010/0200637 A1* | 8/2010 | Beetel | A61B 17/0686 227/175.1 |
| 2010/0224668 A1 | 9/2010 | Fontayne et al. | |
| 2010/0230465 A1 | 9/2010 | Smith et al. | |
| 2010/0258611 A1 | 10/2010 | Smith et al. | |
| 2010/0264195 A1 | 10/2010 | Bettuchi | |
| 2010/0292691 A1* | 11/2010 | Brogna | A61B 18/1445 606/45 |
| 2010/0327041 A1 | 12/2010 | Milliman et al. | |
| 2011/0011916 A1 | 1/2011 | Levine | |
| 2011/0022032 A1* | 1/2011 | Zemlok | A61B 17/07207 606/1 |
| 2011/0060249 A1* | 3/2011 | Schulze | G01L 5/226 600/587 |
| 2011/0095069 A1* | 4/2011 | Patel | A61B 17/1155 227/180.1 |
| 2011/0114697 A1 | 5/2011 | Baxter, III et al. | |
| 2011/0114700 A1 | 5/2011 | Baxter, III et al. | |
| 2011/0125138 A1* | 5/2011 | Malinouskas | A61B 90/98 606/1 |
| 2011/0144640 A1 | 6/2011 | Heinrich et al. | |
| 2011/0147432 A1 | 6/2011 | Heinrich et al. | |
| 2011/0192882 A1 | 8/2011 | Hess et al. | |
| 2011/0218484 A1* | 9/2011 | Zemlok | A61M 13/003 604/26 |
| 2011/0282170 A1* | 11/2011 | Bannerjee | A61B 5/14552 600/341 |
| 2012/0012638 A1* | 1/2012 | Huang | A61B 17/115 227/176.1 |
| 2012/0016413 A1* | 1/2012 | Timm | A61B 17/07207 606/220 |
| 2012/0078278 A1* | 3/2012 | Bales, Jr. | A61B 17/320092 606/169 |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0203213 A1* | 8/2012 | Kimball | A61B 17/320068 606/1 |
| 2012/0228358 A1* | 9/2012 | Zemlok | A61B 90/90 227/176.1 |
| 2012/0232339 A1 | 9/2012 | Csiky | |
| 2012/0273548 A1 | 11/2012 | Ma et al. | |
| 2012/0277790 A1* | 11/2012 | Zemlok | A61B 17/072 606/205 |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |
| 2013/0032628 A1 | 2/2013 | Li et al. | |
| 2013/0056516 A1 | 3/2013 | Viola | |
| 2013/0060258 A1 | 3/2013 | Giacomantonio | |
| 2013/0069088 A1* | 3/2013 | Speck | H01L 33/385 257/E33.059 |
| 2013/0072982 A1* | 3/2013 | Simonson | A61B 17/7083 606/267 |
| 2013/0105544 A1 | 5/2013 | Mozdzierz et al. | |
| 2013/0105546 A1 | 5/2013 | Milliman et al. | |
| 2013/0105551 A1 | 5/2013 | Zingman | |
| 2013/0126580 A1 | 5/2013 | Smith et al. | |
| 2013/0153630 A1 | 6/2013 | Miller et al. | |
| 2013/0153631 A1 | 6/2013 | Vasudevan et al. | |
| 2013/0153633 A1 | 6/2013 | Casasanta, Jr. et al. | |
| 2013/0153634 A1 | 6/2013 | Carter et al. | |
| 2013/0153638 A1 | 6/2013 | Carter et al. | |
| 2013/0153639 A1 | 6/2013 | Hodgkinson et al. | |
| 2013/0175315 A1 | 7/2013 | Milliman | |
| 2013/0175318 A1 | 7/2013 | Felder et al. | |
| 2013/0175319 A1 | 7/2013 | Felder et al. | |
| 2013/0175320 A1 | 7/2013 | Mandakolathur Vasudevan et al. | |
| 2013/0181035 A1 | 7/2013 | Milliman | |
| 2013/0181036 A1 | 7/2013 | Olson et al. | |
| 2013/0186930 A1 | 7/2013 | Wenchell et al. | |
| 2013/0193185 A1 | 8/2013 | Patel | |
| 2013/0193187 A1 | 8/2013 | Milliman | |
| 2013/0193190 A1 | 8/2013 | Carter et al. | |
| 2013/0193191 A1 | 8/2013 | Stevenson et al. | |
| 2013/0193192 A1 | 8/2013 | Casasanta, Jr. et al. | |
| 2013/0200131 A1 | 8/2013 | Racenet et al. | |
| 2013/0206816 A1 | 8/2013 | Penna | |
| 2013/0214027 A1 | 8/2013 | Hessler et al. | |
| 2013/0214028 A1 | 8/2013 | Patel et al. | |
| 2013/0228609 A1 | 9/2013 | Kostrzewski | |
| 2013/0240597 A1 | 9/2013 | Milliman et al. | |
| 2013/0240600 A1 | 9/2013 | Bettuchi | |
| 2013/0248581 A1 | 9/2013 | Smith et al. | |
| 2013/0270814 A1* | 10/2013 | Anton | F16L 19/05 285/93 |
| 2013/0277411 A1 | 10/2013 | Hodgkinson et al. | |
| 2013/0277412 A1 | 10/2013 | Gresham et al. | |
| 2013/0282024 A1* | 10/2013 | Blumenkranz | A61B 34/71 606/130 |
| 2013/0284792 A1 | 10/2013 | Ma | |
| 2013/0291654 A1* | 11/2013 | Blumenkranz | A61B 34/37 73/862.045 |
| 2013/0292449 A1 | 11/2013 | Bettuchi et al. | |
| 2013/0299553 A1 | 11/2013 | Mozdzierz | |
| 2013/0299554 A1 | 11/2013 | Mozdzierz | |
| 2013/0306112 A1* | 11/2013 | Blumenkranz | A61B 90/70 134/34 |
| 2013/0306701 A1 | 11/2013 | Olson | |
| 2013/0306707 A1 | 11/2013 | Viola et al. | |
| 2014/0008413 A1 | 1/2014 | Williams | |
| 2014/0012289 A1* | 1/2014 | Snow | A61B 17/07207 606/130 |
| 2014/0012317 A1 | 1/2014 | Orban et al. | |
| 2014/0037464 A1* | 2/2014 | Kochan, Jr. | G01F 23/18 417/44.2 |
| 2014/0088614 A1* | 3/2014 | Blumenkranz | A61B 34/71 73/862.621 |
| 2014/0110455 A1* | 4/2014 | Ingmanson | A61B 17/068 227/176.1 |
| 2014/0175149 A1* | 6/2014 | Smith | A61B 90/90 227/175.2 |
| 2014/0188101 A1* | 7/2014 | Bales, Jr. | A61B 18/1445 606/33 |

(56) References Cited

U.S. PATENT DOCUMENTS

| | | | |
|---|---|---|---|
| 2014/0249557 A1* | 9/2014 | Koch, Jr. | A61B 90/98 606/170 |
| 2014/0276735 A1* | 9/2014 | Boudreaux | A61B 18/148 606/33 |
| 2014/0358129 A1* | 12/2014 | Zergiebel | A61B 17/320016 606/1 |
| 2015/0005768 A1* | 1/2015 | Sutherland | A61B 18/1442 606/42 |
| 2015/0014393 A1* | 1/2015 | Milliman | A61B 17/1155 227/180.1 |
| 2015/0048139 A1* | 2/2015 | Penna | H05K 5/069 227/176.1 |
| 2015/0048140 A1* | 2/2015 | Penna | A61B 17/1155 227/176.1 |
| 2015/0157354 A1* | 6/2015 | Bales, Jr. | B06B 1/0223 606/169 |
| 2015/0216525 A1* | 8/2015 | Collins | A61B 90/98 227/176.1 |
| 2015/0351765 A1* | 12/2015 | Valentine | A61B 17/07207 227/176.1 |
| 2015/0351819 A1* | 12/2015 | Gustafson | A61B 17/8875 606/104 |
| 2016/0066916 A1* | 3/2016 | Overmyer | G06F 1/266 227/176.1 |
| 2016/0100839 A1* | 4/2016 | Marczyk | A61B 90/98 227/175.3 |
| 2016/0143641 A1 | 5/2016 | Sapienza et al. | |
| 2016/0157856 A1 | 6/2016 | Williams et al. | |
| 2016/0174988 A1 | 6/2016 | D'Agostino et al. | |
| 2016/0174998 A1* | 6/2016 | Lal | A61B 5/685 606/169 |
| 2016/0220150 A1* | 8/2016 | Sharonov | A61B 17/105 |
| 2016/0249921 A1* | 9/2016 | Cappola | A61B 17/07207 227/175.1 |
| 2016/0249928 A1* | 9/2016 | Cappola | A61B 17/07207 227/176.1 |
| 2016/0265938 A1* | 9/2016 | Hryb | A61B 17/1155 |
| 2016/0273687 A1* | 9/2016 | Rubinski | F16L 19/103 |
| 2016/0302792 A1 | 10/2016 | Motai | |
| 2016/0374672 A1* | 12/2016 | Bear | H02J 7/00 606/219 |
| 2017/0079640 A1* | 3/2017 | Overmyer | H02P 7/06 |
| 2018/0042610 A1* | 2/2018 | Sgroi, Jr. | A61B 17/07207 |
| 2018/0067003 A1* | 3/2018 | Michiwaki | G01L 1/22 |
| 2018/0092710 A1* | 4/2018 | Bosisio | A61C 5/42 |
| 2018/0116667 A1* | 5/2018 | Bae | A61B 17/1155 |
| 2018/0243042 A1* | 8/2018 | Eschbach | A61B 17/07207 |
| 2018/0353185 A1* | 12/2018 | Nicholas | A61B 17/07207 |
| 2018/0360460 A1* | 12/2018 | Mozdzierz | A61B 17/3476 |
| 2019/0125432 A1* | 5/2019 | Shelton, IV | A61B 17/06066 |
| 2019/0125459 A1* | 5/2019 | Shelton, IV | A61B 17/0206 |
| 2019/0154526 A1* | 5/2019 | Burrow | G01B 1/2262 |
| 2019/0174636 A1* | 6/2019 | Sgroi, Jr. | B29C 45/14549 |
| 2019/0200977 A1* | 7/2019 | Shelton, IV | A61B 17/07207 |
| 2019/0200981 A1* | 7/2019 | Harris | B25J 13/006 |
| 2019/0201029 A1* | 7/2019 | Shelton, IV | A61B 17/0206 |
| 2019/0201030 A1* | 7/2019 | Shelton, IV | A61B 17/1285 |
| 2019/0206565 A1* | 7/2019 | Shelton, IV | A61B 34/37 |
| 2020/0054337 A1* | 2/2020 | Sgroi, Jr. | A61B 17/1155 |
| 2020/0088592 A1* | 3/2020 | Burrow | G01L 1/2206 |
| 2020/0093484 A1* | 3/2020 | Shelton, IV | G01B 7/24 |
| 2020/0405304 A1* | 12/2020 | Mozdzierz | A61B 17/072 |
| 2021/0128019 A1* | 5/2021 | Pearlman | G01L 1/2218 |
| 2021/0128153 A1* | 5/2021 | Sgroi | A61B 90/98 |
| 2022/0283047 A1* | 9/2022 | Ogawa | G01L 5/166 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2777518 A1 | 9/2014 |
| EP | 3315082 A1 | 5/2018 |
| EP | 3415102 A2 | 12/2018 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013510971 A * | 3/2013 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

RELOAD ASSEMBLY INJECTION MOLDED STRAIN GAUGE

FIELD

This disclosure is generally related to surgical stapling devices and, more particularly, to surgical stapling devices that include a reload assembly having a strain gauge for measuring different parameters related to stapling and/or cutting of tissue.

BACKGROUND

Powered surgical stapling devices include a handle assembly, an adaptor assembly including a distal portion supported on the handle assembly, and a tool assembly supported on the distal portion of the adaptor assembly. The stapling device may also include a strain gauge for measuring characteristics of tissue being stapled, e.g., tissue thickness, tissue compression, etc., and/or parameters related to staple formation or tissue cutting, e.g., cutting force, firing force, etc. Typically, a strain gauge is supported within the adaptor assembly and is formed from electronics that can be sterilized or reprocessed to facilitate reuse of the adaptor assembly. Such electronics are costly.

SUMMARY

The techniques of this disclosure generally relate to surgical stapling devices and in particular to circular stapling devices for performing end to end anastomoses and similar suturing procedures.

One aspect of the disclosure is directed to a reload assembly including a shell housing, a staple cartridge, a plurality of staples, a staple pushing member, a knife carrier, and a knife. The shell housing supports a strain gauge and includes a distal portion, a proximal portion, and an outer housing portion defining a cavity. The staple cartridge is supported on the distal portion of the shell housing and the plurality of staples is received within the staple cartridge. The staple pushing member is supported within the cavity defined by the shell housing and defines a through bore. The knife carrier is supported within the through bore of the staple pushing member and is movable between retracted and advanced positions. The knife is supported on the knife carrier and is movable with the knife carrier between the retracted and advanced positions.

Another aspect of the disclosure is directed to a stapling device including a handle assembly, an adaptor assembly, and a reload assembly. The adaptor assembly has a proximal portion supported on the handle assembly and a distal portion. The reload assembly includes a shell housing, a staple cartridge, a plurality of staples, a staple pushing member, a knife carrier, and a knife. The shell housing supports a strain gauge and includes a distal portion, a proximal portion, and an outer housing portion defining a cavity. The staple cartridge is supported on the distal portion of the shell housing and the plurality of staples is received within the staple cartridge. The staple pushing member is supported within the cavity defined by the shell housing and defines a through bore. The knife carrier is supported within the through bore of the staple pushing member and is movable between retracted and advanced positions. The knife is supported on the knife carrier and is movable with the knife carrier between the retracted and advanced positions.

In aspects of the disclosure, the outer housing portion has a tubular extension and the strain gauge is supported on the tubular extension.

In some aspects of the disclosure, the strain gauge is molded into the tubular extension of the shell housing.

In certain aspects of the disclosure, the staple cartridge and the knife have an annular configuration.

In aspects of the disclosure, a coupling mechanism is supported about the tubular extension of the shell housing and is adapted to secure the reload assembly to a surgical stapling device.

In some aspects of the disclosure, the reload assembly includes a staple actuator that is positioned within the cavity defined by the shell housing in abutting relation to the staple pushing member, wherein the staple actuator is movable from a retracted position to an advanced position to move the staple pushing member from its retracted position to its advanced position.

The details of one or more aspects of the disclosure are set forth in the accompanying drawings and the description below. Other features, objects, and advantages of the reload assembly described in this disclosure will be apparent from the description and drawings, and from the claims.

BRIEF DESCRIPTION OF DRAWINGS

Various aspects and features of the disclosure are described with reference to the drawings wherein like numerals designate identical or corresponding elements in each of the several views and.

DETAILED DESCRIPTION

In this description, the term "proximal" is used generally to refer to that portion of the device that is closer to a clinician, while the term "distal" is used generally to refer to that portion of the device that is farther from the clinician. Further, the term "clinician" is used generally to refer to medical personnel including doctors, nurses, and support personnel.

Figure 1:
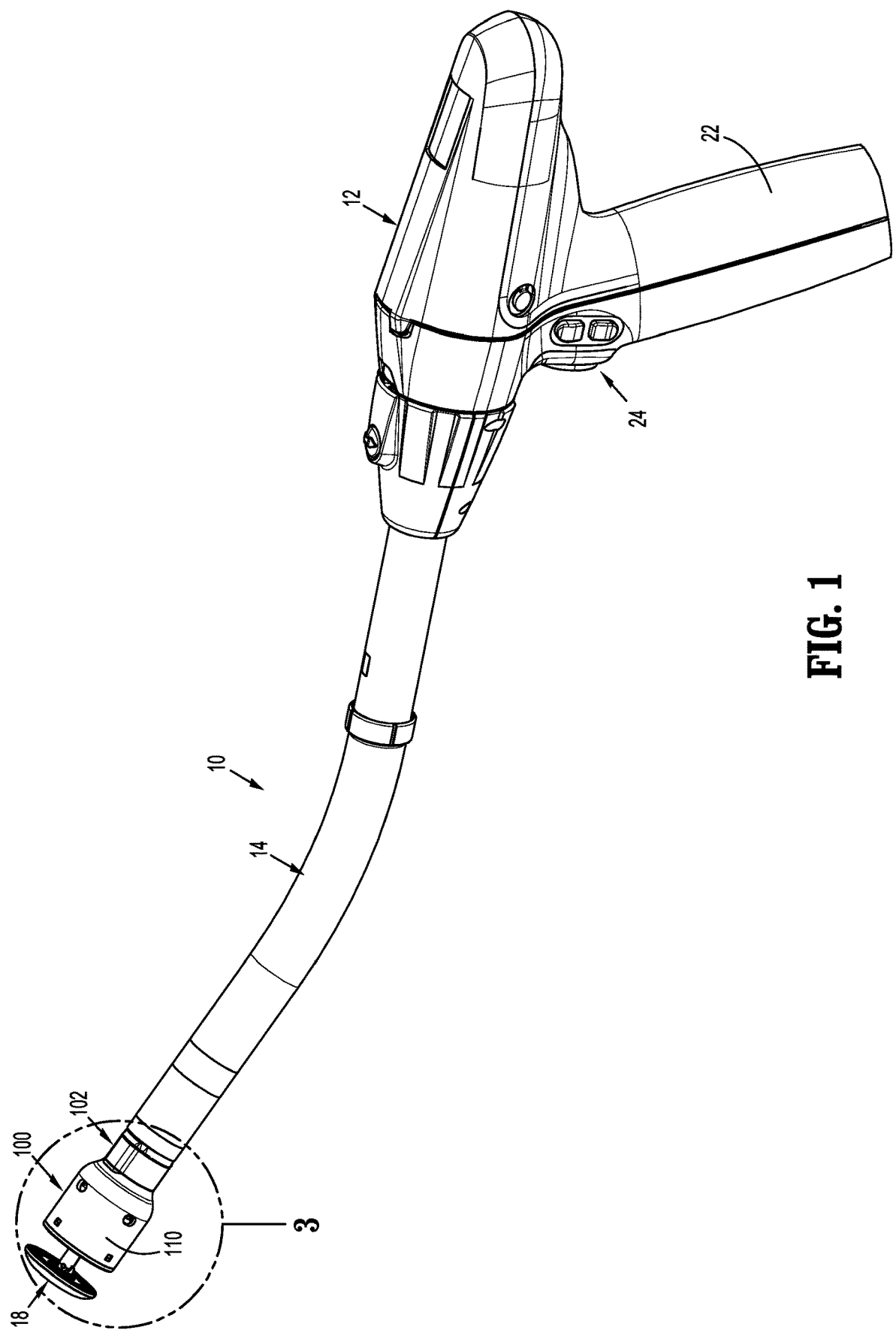
FIG. 1 is a side perspective view of a surgical stapling device including a tool assembly with a reload assembly including aspects of the disclosure in an unclamped position.
Figure 8:
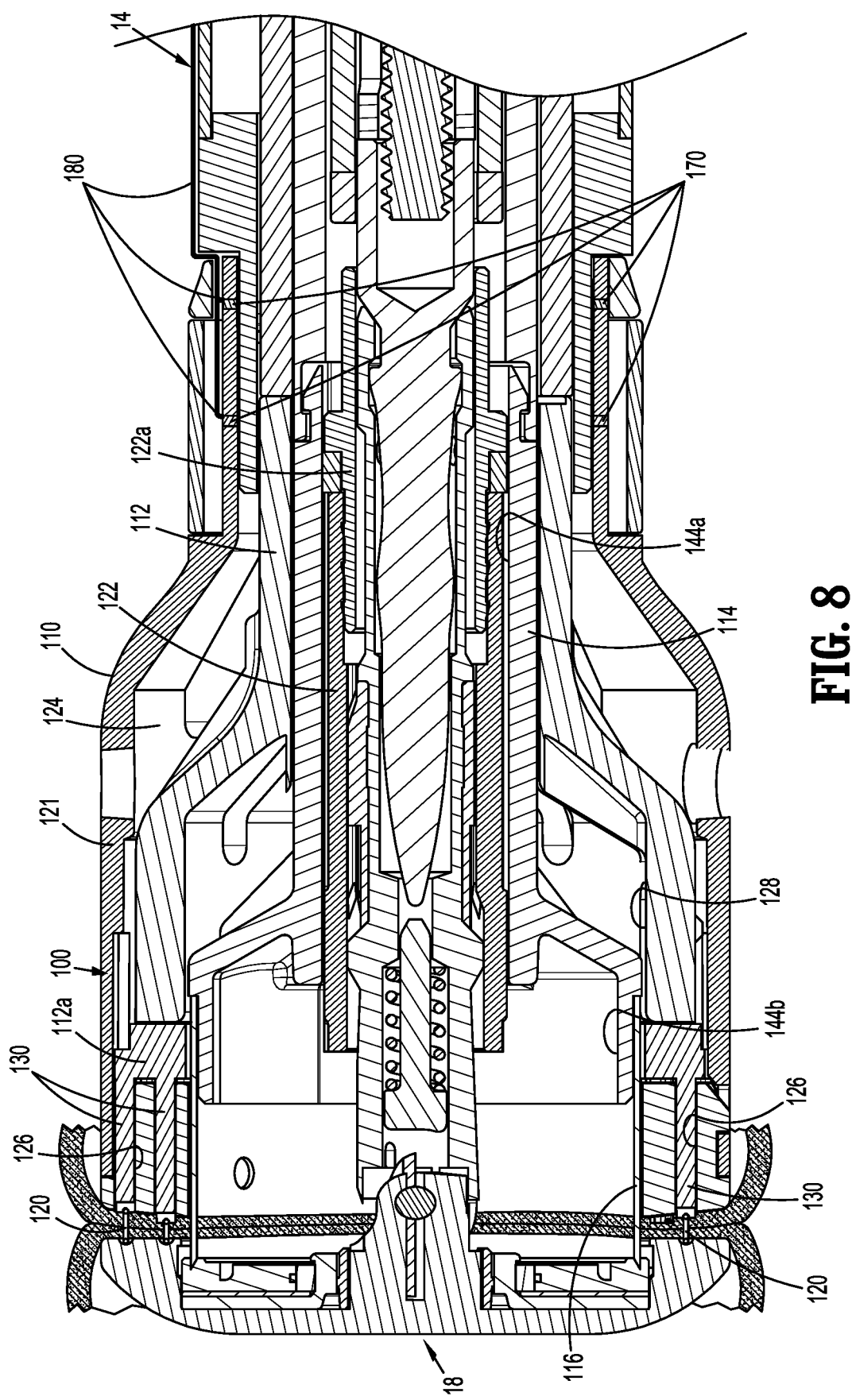
FIG. 8 is a side cross-sectional view of the tool assembly shown in FIG. 1 with the tool assembly in a clamped and fired position.

FIG. 1 illustrates a circular stapling device 10 including a reload assembly in accordance with exemplary aspects of the disclosure shown generally as a reload assembly 100. The circular stapling device 10 includes a handle assembly 12, an elongate body or adaptor assembly 14, the reload assembly 100, and an anvil assembly 18 that is supported for movement in relation to the reload assembly 100 between an open position (FIG. 1) and a clamped position (FIG. 8). The reload assembly 100 includes a proximal portion 102 that can be releasably coupled to a distal portion 14a of the adaptor assembly 14 and the adaptor assembly 14 includes a proximal portion 14b that can be releasably coupled to the handle assembly 12. The handle assembly 12 includes a stationary grip 22 that supports actuation buttons 24 for controlling operation of various functions of the circular stapling device 10 including approximation of the reload assembly 100 and anvil assembly 18, firing of staples from the reload assembly 100, and cutting or coring of tissue as described in further detail below.

The circular stapling device 10 is illustrated as an electrically powered stapling device including an electrically powered handle assembly 12 that may support one or more batteries (not shown). The adaptor assembly 14 translates power from the handle assembly 12 to the reload and anvil assemblies 100, 18, respectively, to staple and cut tissue. Examples of electrically powered stapling devices can be found in U.S. Pat. Nos. 9,055,943, 9,023,014, and U.S. Publication Nos. 2018/0125495, and 2017/0340351. Alternately, it is envisioned that aspects of the reload assembly disclosed herein could also be incorporated into a manually powered stapling device such as disclosed in, e.g., U.S. Pat. No. 7,303,106 (the '106 Patent), or a stapling device that is configured for use with a robotic system as disclosed in, e.g., U.S. Pat. No. 9,962,159, that does not include a handle assembly.

Figure 2:
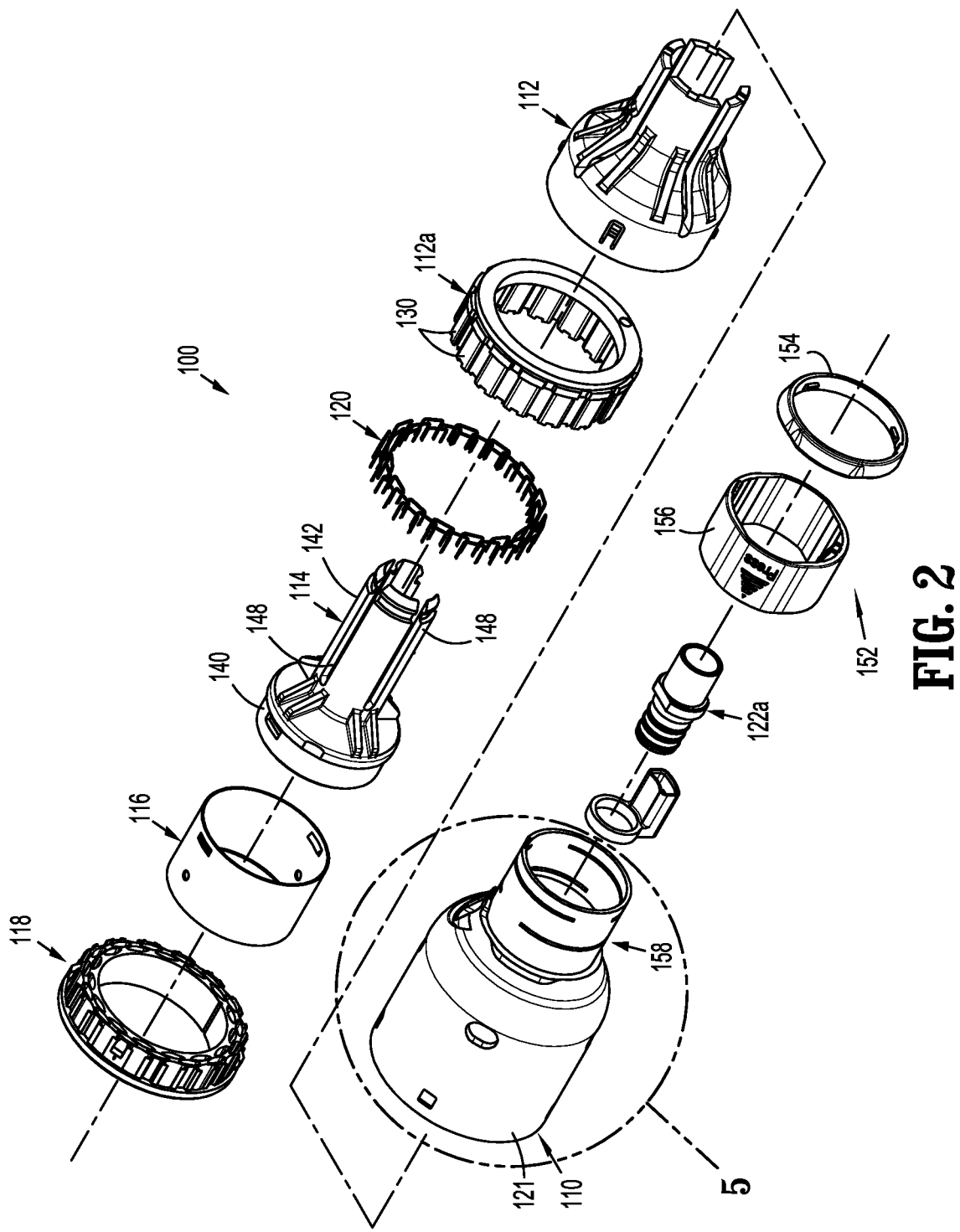
FIG. 2 is a side perspective exploded view of the shell assembly of the tool assembly shown in FIG. 2.

FIG. 2 illustrates an exploded view of the reload assembly 100 which includes a shell housing 110, a staple actuator 112, a staple pushing member 112a, a knife carrier 114, an annular knife 116 supported on the knife carrier 114, a staple cartridge 118, and a plurality of staples 120 supported within the staple cartridge 118. The shell housing 110 includes an outer housing portion 121 and an inner housing portion 122 (FIG. 8) that are spaced from each other to define an annular cavity 124 (FIG. 8) positioned between the outer and inner housing portions 121 and 122. The inner housing portion 122 supports a bushing 122a that provides stability to the shell housing 110. The staple actuator 112 and the staple pushing member 112a are movable within the annular cavity 124 of the shell housing 110 from a retracted position to an advanced position to eject the staples 120 from the staple cartridge 118 as described in further detail below.

The staple cartridge 118 is annular and defines an annular array of staple pockets 126 (FIG. 8). Each of the staple pockets 126 supports one of the staples 120. The staple actuator 112 and the staple pushing member 112a together define a longitudinal through bore 128 (FIG. 8) that receives the knife carrier 114. The staple actuator 112 has a distal portion that abuts a proximal portion of the staple pushing member 112a such that distal movement of the staple actuator 112 within the shell housing 110 causes distal movement of the staple pushing member 112a within the shell housing 110. The staple pushing member 112a of the reload assembly 100 has a plurality of fingers 130. Each of the plurality of fingers 130 is received within a respective one of the staple pockets 126 of the staple cartridge 118 and is movable through the respective staple pocket 126 to eject the staples 120 from the staple pockets 126 when the staple pushing member 112a is moved from a retracted position to an advanced position within the shell housing 110.

The knife carrier 114 is received within the longitudinal through bore 128 of the staple actuator 112 and includes a distal body portion 140 and a plurality of spaced longitudinally extending proximal body portions 142. The distal body portion 140 and the proximal body portions 142 define a stepped central bore (FIG. 8) having a proximal portion 144a and a distal portion 144b. The proximal portion 144a of the stepped central bore of the knife carrier 114 I received about the inner housing portion 122 of the shell housing 110 such that the knife carrier 114 is movable within the staple actuator 112 about the inner housing portion 122 of the shell housing 110 between a retracted position and an advanced position (FIG. 8). The distal body portion 140 of the knife carrier 114 includes a plurality of longitudinal extensions 146. The proximal body portions 142 of the knife carrier 114 defines slots 148 that receive guide portions (not shown) of the shell housing 110 to limit the knife carrier 114 to longitudinal movement within the shell housing 110.

Figure 3:
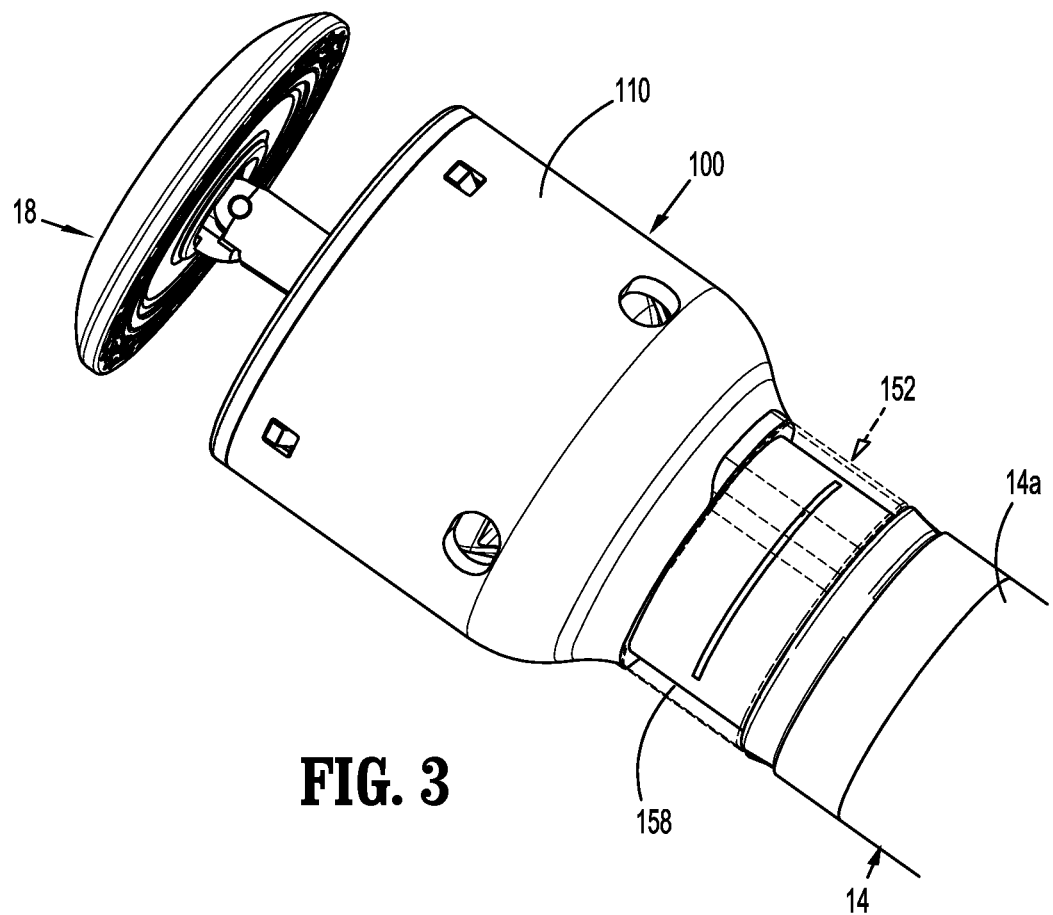
FIG. 3 is an enlarged view of indicted area of detail shown in FIG. 1.
Figure 4:
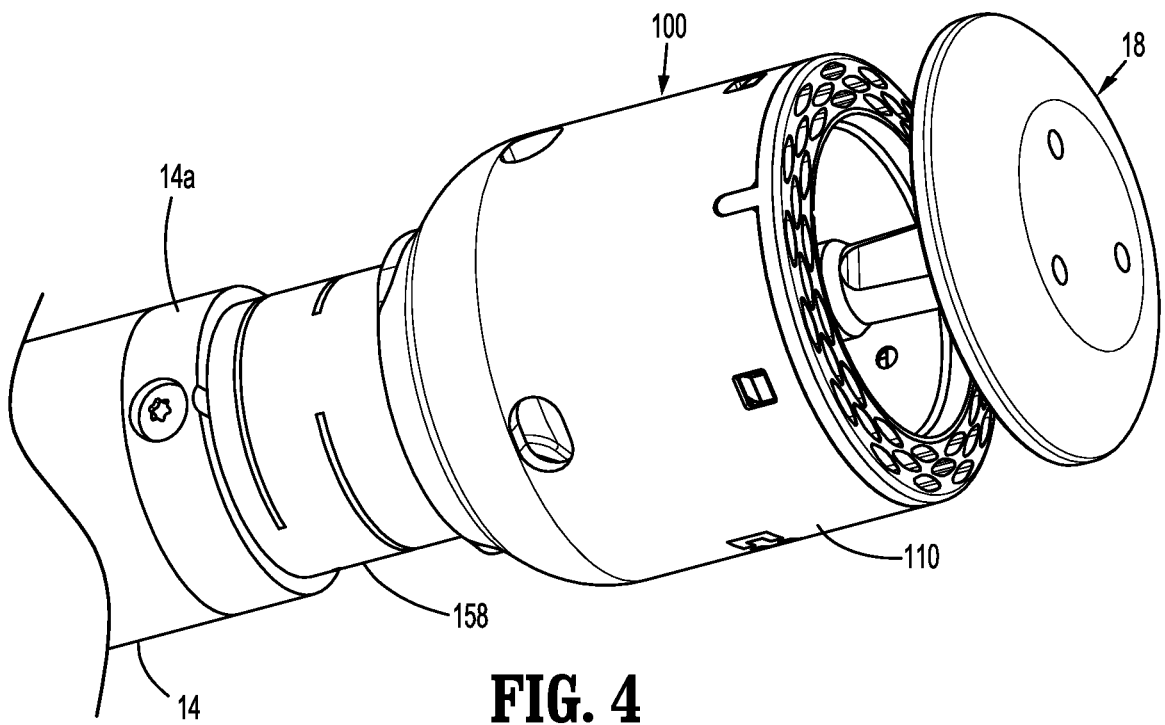
FIG. 4 is a side perspective view of the tool assembly shown in FIG. 1 in the unclamped position with the coupling mechanism of the reload assembly removed.
Figure 5:
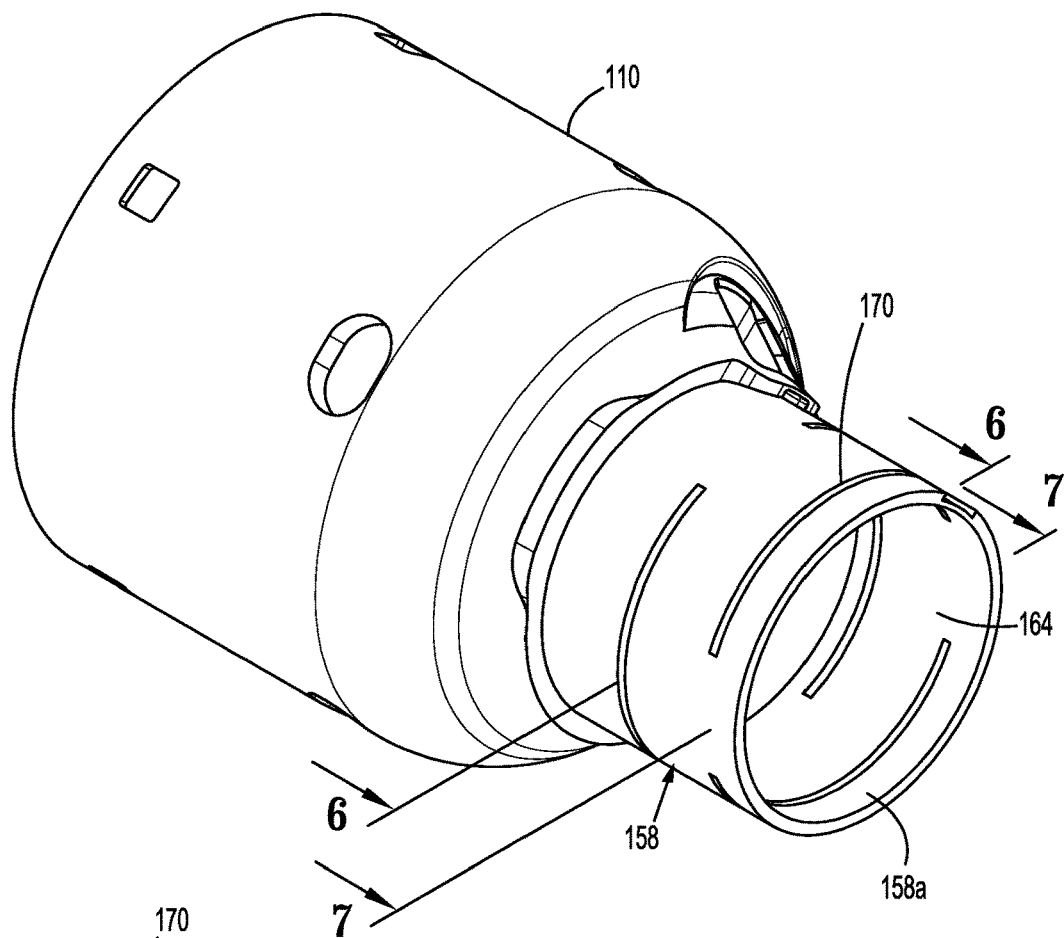
FIG. 5 is an enlarged view of the indicated area of detail shown in FIG. 2.
Figure 6:
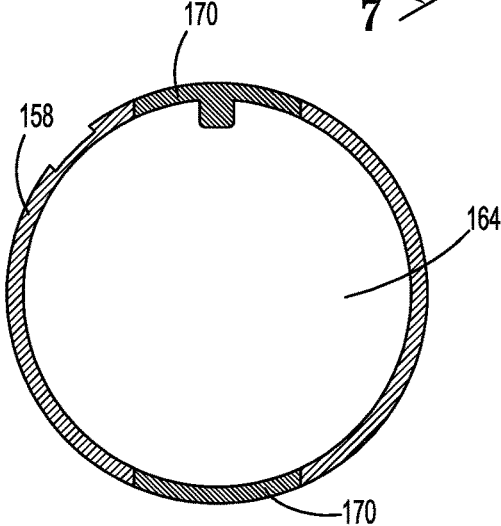
FIG. 6 is a cross-sectional view taken along section line 6-6 of FIG. 5.
Figure 7:
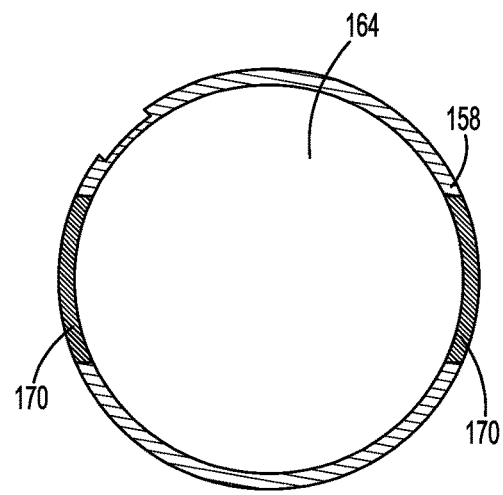
FIG. 7 is a cross-sectional view taken along section line 7-7 of FIG. 5.

The shell housing 110 includes a proximal portion 150 that supports a coupling mechanism 152 (FIG. 3). The coupling mechanism 152 is operable to releasably couple the reload assembly 100 to the adaptor assembly 14 of the stapling device 10 (FIG. 1) to facilitate replacement of the reload assembly 100 and reuse of the stapling device 10. The coupling mechanism 152 includes a retaining member 154 and a coupling member 156. The coupling member 156 is received about a proximal portion 158 of the shell housing 110 and is configured to engage the distal portion of the adaptor assembly 14 (FIG. 1) to couple the adaptor assembly 14 to the reload assembly 100. It is envisioned that other types of coupling mechanisms can be used to secure the reload assembly 100 to the distal portion of the adaptor assembly 14.

The reload assembly 100 may include an e-prom holder 160 (FIG. 2) that is supported on the shell housing 110 to support an e-prom (not shown). As is known in the art, an e-prom communicates with the adaptor assembly 14 to provide information to the adaptor assembly 14 and the handle assembly 12 related to characteristics of the reload assembly 10.

In certain aspects of the disclosure, the reload assembly 110 of the stapling device 10 designed to be disposable and the handle assembly 12 and the adaptor assembly 14 are designed to be reprocessed or resterilized and reused. As such, the reload assembly 100 and components that form the reload assembly 100 are formed of materials, e.g., plastics, that are less costly and less durable than materials e.g., stainless steel, used to form the handle assembly 12 and the adaptor assembly 14.

FIGS. 2-7 illustrate the proximal portion 158 of the shell housing 110 of the reload assembly 100. The shell housing 110 of the reload assembly 100 is molded of a plastic material, e.g., polycarbonate, polyethylene, nylon, etc. . . . . . The proximal portion 158 of the shell housing 110 includes a tubular extension 158a of the outer housing portion 121 of the shell housing 110. The tubular extension 158a defines a cylindrical cavity 164 that is dimensioned to receive the distal portion 14a (FIG. 1) of the adaptor assembly 14. The coupling mechanism 152 is supported about the tubular extension 158a of the proximal portion 158 of the shell housing 110 and is operable to secure the reload assembly 100 to the adaptor assembly 14.

The shell housing 110 of the reload assembly 100 supports a strain gauge 170. In one aspect of the disclosure, the strain gauge 170 includes one or more components that are molded into the shell housing 110 of the reload assembly 100 and is disposable with the reload assembly 100 after the reload assembly 100 is fired. In certain aspects of the disclosure, the strain gauge 170 is molded into the tubular extension 158a of the proximal portion 158 of the shell housing 110. It is envisioned, however, that the strain gauge 170 could be molded or supported on or within other portions of the shell housing 110 or reload assembly 100.

As illustrated in FIG. 8, the strain gauge 170 is connected to a processor (not shown) located in the handle assembly 12 (FIG. 1) by wires 180. When the reload assembly 100 is in a clamped position and is fired, the firing and clamping forces are translated through the shell housing 100 and through the strain gauge 170 to effect a change in a circuit defined by the strain gauge 170 and the electrical wires 180. The processor interprets this change to identify certain parameters related to the characteristics of the tissue and/or clamping and firing conditions. As described above, the strain gauge is formed of inexpensive materials to facilitate disposal of the reload assembly 100 after use.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A reload assembly comprising:
   a shell housing including an outer housing portion defining a cavity and having a proximal portion and a distal portion, the outer housing portion having a tubular extension that forms a proximal-most portion of the proximal portion of the outer housing portion of the shell housing and is configured to receive a distal portion of a stapling device, the proximal-most portion of the outer housing portion having a diameter that is smaller than a diameter of the distal portion of the outer housing;
   a strain gauge molded into the tubular extension of the shell housing;
   a staple cartridge supported on the distal portion of the shell housing and having an annular configuration;
   a plurality of staples received within the staple cartridge;
   a staple pushing member supported within the cavity defined by the shell housing, the staple pushing member defining a through bore;
   a knife carrier supported within the through bore of the staple pushing member, the knife carrier being movable between retracted and advanced positions;
   a knife supported on the knife carrier, the knife being movable with the knife carrier between the retracted and advanced positions and having an annular configuration; and
   a coupling mechanism extending about the tubular extension of the shell housing, the coupling mechanism adapted to secure the reload assembly to a stapling device, the reload assembly being separable from the adaptor assembly such that the reload assembly including the strain gauge is disposable;
   wherein the strain gauge is positioned such that when the reload assembly is clamped and fired, firing and clamping forces are translated through the shell housing and through the strain gauge.

2. The reload assembly of claim 1, further including a staple actuator, the staple actuator positioned within the cavity defined by the shell housing in abutting relation to the staple pushing member, the staple actuator movable from a retracted position to an advanced position to move the staple pushing member from its retracted position to its advanced position.

3. The reload assembly of claim 1, wherein the staple cartridge defines an annular array of staple pockets and the staple pushing member includes a plurality of fingers that are received within the annular array of staple pockets, each of the plurality of staples received within one of the annular array of staple pockets such that movement of the staple pushing member from its retracted position to its advanced position ejects the plurality of staples from the staple cartridge.

4. A stapling device comprising:
   a handle assembly;
   an adaptor assembly having a proximal portion and a distal portion, the proximal portion supported on the handle assembly; and
   a reload assembly releasably coupled to the distal portion of the adaptor assembly, the reload assembly including a shell housing, a staple cartridge, a plurality of staples, a staple pushing member, a knife carrier, a knife, and a coupling mechanism, the shell housing including an outer housing portion defining a cavity and having a proximal portion and a distal portion, the outer housing portion including a tubular extension that forms a proximal-most portion of the proximal portion of the outer housing portion of the shell housing and receives the distal portion of the adaptor assembly, the coupling mechanism extending about the tubular extension of the shell housing and releasably securing the reload assembly to the adaptor assembly, the proximal-most portion of the outer housing portion having a diameter that is smaller than a diameter of the distal portion of the outer housing, a strain gauge molded into the tubular extension, the staple cartridge supported on the distal portion of the shell housing and having an annular configuration, the plurality of staples received within the staple cartridge, the staple pushing member supported within the cavity defined by the shell housing and defining a through bore, the knife carrier supported within the through bore of the staple pushing member and being movable between retracted and advanced positions, the knife supported on the knife carrier and being movable with the knife carrier between the retracted and advanced positions, the knife having an annular configuration, wherein the strain gauge is positioned such that when the reload assembly is clamped and fired, firing and clamping forces are translated through the shell housing and through the strain gauge, the reload assembly being separable from the adaptor assembly such that the reload assembly including the strain gauge is disposable.

5. The stapling device of claim 4, further including a staple actuator, the staple actuator positioned within the cavity defined by the shell housing in abutting relation to the staple pushing member, the staple actuator movable from a retracted position to an advanced position to move the staple pushing member from its retracted position to its advanced position.

6. The stapling device of claim 4, wherein the staple cartridge defines an annular array of staple pockets and the staple pushing member includes a plurality of fingers that are received within the annular array of staple pockets, each of the plurality of staples received within one of the annular array of staple pockets such that movement of the staple pushing member from its retracted position to its advanced position ejects the plurality of staples from the staple cartridge.

<p style="text-align:center">* * * * *</p>